United States Patent
Hartl et al.

(10) Patent No.: US 6,844,375 B2
(45) Date of Patent: Jan. 18, 2005

(54) 4-METHYLENE-1,3-DIOXOLANES AS CROSS-LINKING AGENTS

(75) Inventors: Helmut Hartl, Berlin (DE); Rainer B. Frings, Berlin (DE); Gerwald F. Grahe, Berlin (DE)

(73) Assignee: Dainippon Ink and Chemicals, Inc., Tokyo (JP)

( * ) Notice: Subject to any disclaimer, the term of this patent is extended or adjusted under 35 U.S.C. 154(b) by 254 days.

(21) Appl. No.: 09/934,655

(22) Filed: Aug. 23, 2001

(65) Prior Publication Data

US 2002/0045674 A1 Apr. 18, 2002

(30) Foreign Application Priority Data

Aug. 25, 2000 (EP) .......................................... 00118116

(51) Int. Cl.⁷ .......................... C08F 2/46; C07D 317/00
(52) U.S. Cl. .......................... 522/169; 522/168; 522/49; 522/68; 522/150; 522/154; 428/411.1; 549/455; 549/450; 549/453; 549/454; 549/429; 549/430; 549/435
(58) Field of Search .................. 522/168, 169, 522/150, 154, 68, 49; 428/411.1; 549/455, 450, 453, 454, 429, 430, 435

(56) References Cited

FOREIGN PATENT DOCUMENTS

DE    906514    *  3/1954
GB    724032       2/1955

OTHER PUBLICATIONS

Latvijas PSR Zinatnu Akademijas Vestis, (6), 667–72, 1994. (abstract only).*
ASC abstract No. 52:59140 to Ortho, Hans (corresponds to DE 906514).*
Angewandte Chemie, No. 19/20, (1962), pp. 544–552 (XP–000881967).
XP–002157177; "6001 Chemical Abstracts, Columbus, Ohio, US"; vol. 65, No. 38; 1965.
XP–002157178; "6001 Chemical Abstracts, Columbus, Ohio, US"; vol. 86, No. 15; 1977.
XP–002157179, "6001 Chemical Abstracts, Columbus Ohio, US"; vol. 77, No. 1; 1972.

* cited by examiner

Primary Examiner—James J. Seidleck
Assistant Examiner—Sanza L. McClendon
(74) Attorney, Agent, or Firm—Armstrong, Kratz, Quintos, Hanson & Brooks, LLP

(57) ABSTRACT

The invention relates to: 4-methylene-1,3-dioxolanes of the general formula (I)

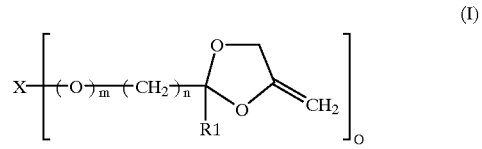

(I)

wherein R1 denotes hydrogen, $C_5$–$C_6$-cycloalkyl or $C_1$–$C_4$-alkyl; m and n, which may be the same or different, denote 0 or 1, whereby $m \leq n$, o denotes 2, 3 or 4 depending on the valency of the group X; and X denotes a C—C single bond, straight-chain or branched $C_1$–$C_{18}$-alkylene, $C_5$–$C_6$-cycloalkylene, $C_8$–$C_{18}$-arylalkylene, —$CH_2(OCH_2CH_2)_pOCH_2$—, —$CH_2(OCH(CH_3)CH_2)_pOCH_2$—, wherein p is an integer from 0 to 100; a process for their production; and intermediate products used. Moreover, compositions capable of emission-free, photocationic cross-linking, which comprise 4-methylene-1,3-dioxolanes of the general formula (I) and their use for the production of solvent-resistant and transparent films.

17 Claims, No Drawings

4-METHYLENE-1,3-DIOXOLANES AS CROSS-LINKING AGENTS

FIELD OF THE INVENTION

The invention relates to compounds with two or more 4-methylene-1,3-dioxolane groups, their production and intermediate products therefrom, and the photocationic cross-linking of these monomers.

BACKGROUND OF THE INVENTION

Commercially available vinyl ethers are produced by means of the base-catalysed addition of acetyl groups onto alcohols under pressure. The compounds obtained contain the structural element $H_2C=CH—OR$ and have been used technically for many years. These compounds enjoy particular attention in the context of cationic and photocationic polymerisation, because they generally represent very reactive compounds as a result of the number of electrons of their double bond.

However, users continually complain that volatile components with an intense odour are formed during cross-linking, and that in higher concentrations, these are irritants and therefore unsafe with reference to industrial hygiene. For reasons of industrial health and safety, comprehensive precautionary measures are therefore necessary. These not only represent a considerable financial expense for the user, but also increase the cost of the products.

For some time, it has been known that one of the principal components of these undesirable, volatile by-products is acetaldehyde. This occurs in a subsidiary reaction of the vinyl ether with the atmospheric moisture. T. MORIGUCHI et al. describe one possible reaction pathway in *Macromolecules* 1995, 28, 4334–4339.

Various approaches to solving this problem have been under discussion for a considerable time. From an economic perspective, the rearrangement of readily accessible allylethers to isopropenylether using noble metal catalysts seems most promising (J. V. CRIVELLO, U.S. Pat. No. 5,486,545 of Jan. 23, 1996). However, this view overlooks the fact that, like the commercial vinyl ethers, isopropenylether can also enter a subsidiary reaction with water during the cationic and photocationic polymerisation, leading to the formation of propionaldehyde. The demand for an emission-free cross-linking cannot therefore be fulfilled with isopropenylether. In principle, open-chain vinyl ethers are not capable of achieving this because in this case, volatile decomposition products can always be formed in the presence of moisture.

However, cyclic vinyl ethers, such as 2,3-dihydrofuranes and 2,3-dihydropyranes are almost ideal vinyl ethers. During photocationic reaction, they are indeed also capable of entering subsidiary reactions with water, but they do not produce volatile decomposition products because the irritant aldehyde component remains firmly anchored in the molecule. However, the accessibility of these heterocyclic compounds—especially the derivatives with two or more dihydrofurane or dihydropyrane groups which are suitable for cross-linking—is extremely difficult and expensive with regard to the synthesis. As a result, the synthesis of larger quantities has so far not been technically possible on a cost-favourable scale.

By contrast, the class of 4-methylene-1,3-dioxolanes is substantially more accessible. Initial attempts to cross-link 4-methylene-1,3-dioxolanes are described in the U.S. Pat. No. 2,445,733 of Jul. 7, 1945. Depending on the metal ion involved, the Friedel-Crafts catalysts used in this context lead to materials of a reddish-brown color and not to solvent-resistant networks. The use of a solution of zinc chloride in alcohol (H. ORTH, *Angew. Chem.* 1952, 64, 544–553) provided an improvement, but the polymerisations carried out were particularly exothermic and in some cases their course after addition of the catalyst was explosive. However, it must be noted on the positive side that the resulting networks provide considerable surface hardness and associated good processing properties.

More recently, it has become known that 4-methylene-1,3-dioxolanes also exhibit photocationic activity. For instance, K. D BELFIELD and F. B. ABDELRAZZAQ, *Macromolecules* 1997, 30, 6985–88, describe a photocationic cross-linking of 2,2'-(1,4-phenylene)-bis-(4-methylene-1,3-dioxolane) with 2-phenyl-4-methylene-1,3-dioxolane. However, both monomers are of an aromatic nature, i.e. they have aromatic substituents in the 2-position. Now, however, it is known that 4-methylene-1,3-dioxolanes with a 2,2-diphenyl- or 2-phenyl-2-alkyl substitution eliminate the ketone component during polymerisation (R. S. DAVIDSON, G. J. HOWGATE, *J. Photochem. Photobiol. A*, 1997, 109, 185–193 and Y. HIRAGURI, T. ENDO, *J. Polym. Sci. Part A: Polym. Chem.* 1989, 27, 4403–4411), i.e. more or less volatile components are split off. The requirement for emission-free cross-linking can therefore not be fulfilled.

The polymerisation processes provided in the state of the art operate either in a solvent or in a large composition. The duration of the polymerisation is in the range of several hours and the yields are not quantitative. They cannot therefore simply be transferred to photocationic cross-linking especially of films and thin layers.

SUMMARY OF THE INVENTION

An object of the invention is to develop 4-methylene-1,3-dioxolanes suitable for photocationic cross-linking. The compounds should satisfy the following requirements:
(a) no splitting off of acetaldehyde or propionaldehyde during cross-linking,
(b) ready accessibility through technically simple operations,
(c) production from inexpensive starting materials available in technical quantities,
(d) no use of expensive noble metal catalysts or catalyst systems which are difficult to regenerate,
(e) higher activity in comparison with commercial vinyl ethers,
(f) low vapour pressure, so that nuisance caused by bad smell is excluded as much as possible.

Other objects and effects of the present invention will become apparent from the following description.

The present invention provides 4-methylene-1,3-dioxolanes of the general formula (I)

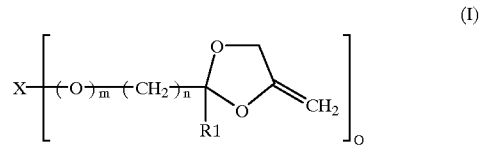

wherein R1 denotes hydrogen, $C_5$–$C_6$-cycloalkyl or $C_1$–$C_4$-alkyl; m and n, which may be the same or different, denote 0 or 1, whereby m≦n, o denotes 2, 3 or 4 depending on the valency of the group X; and X denotes a C—C single bond, straight-chain or branched $C_1$–$C_{18}$-alkylene, $C_5$–$C_6$-cycloalkylene, $C_8$–$C_{18}$-arylalkylene, —$CH_2(OCH_2CH_2)_pOCH_2$—, —$CH_2(OCH(CH_3)CH_2)_pOCH_2$—, wherein p is an integer from 0 to 100, or denotes a group selected from

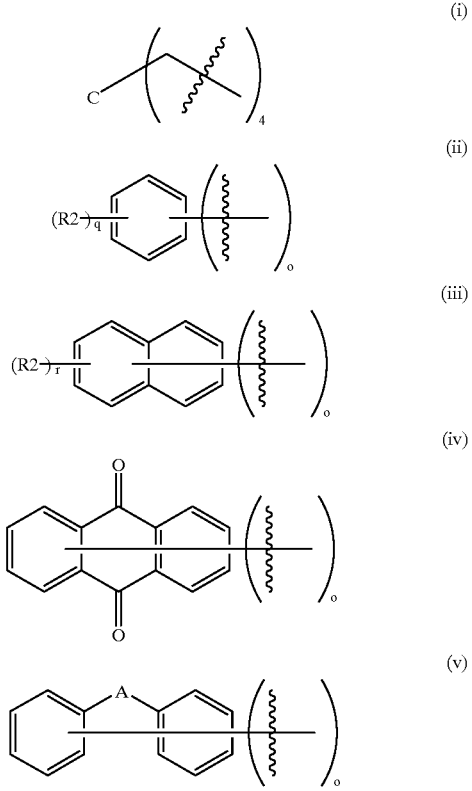

wherein $q \leq (6-o)$, $r \leq (8-o)$, R2 denotes H or a $C_1$–$C_4$-alkyl group and A denotes a single bond or denotes —$C(CH_3)_2$—, —$C(CF_3)_2$—, —$CH_2$—, —$SO_2$— or —(C=O)—, and wherein the 2-position of the 1,3-dioxolane ring is not linked directly to an aromatic group.

DETAILED DESCRIPTION OF THE INVENTION

In the above formulae (i) to (v) for possible groups X, the line interrupted by a wavy line denotes a bond, by means of which the linking to the grouping containing the 4-methylene-1,3-dioxolane group is achieved.

The condition that the 2-position of the 1,3-dioxolane ring is not directly linked to an aromatic group, means that X does not denote one of the groups enumerated in (ii) to (v), if n is zero.

The 4-methylene-1,3-dioxolanes, which can be regarded as 1,1-disubstituted vinyl ethers, fulfil the above-enumerated conditions (a) to (f). Regarding the reactivity of vinyl ethers, it is known that they follow approximately the order $R^1R^2C=$—O—R<$R^1$CH=CH—O—R<$CH_2$=CH—O—R<$CH_2$=$CR^3$—O—R, i.e. that the 1,1-disubstituted vinyl ethers are generally the most reactive if their substituents are not sterically over-demanding (O. NUYKEN, R. B. RAETHER, C. E. SPINDLER, Macromol. Chem. Phys. 1998, 199, 191–196).

The invention is based on the surprising insight that 4-methylene-1,3-dioxolanes exhibit the high reactivity of 1,1-disubstituted vinyl ethers in photocationic reactions in spite of their simultaneously allylic structure (the reluctance of allyl compounds to enter polymerisation reactions is well known).

The following paragraphs explain in greater detail some of the terms which will be used below. Unless otherwise specified, the term "alkyl" denotes a monovalent alkane radical of the general formula $C_nH_{2n+1}$, wherein n denotes the number of carbon atoms and ranges from 1 to 18, preferably from 1 to 6. The alkyl radicals may be straight-chain or branched. Examples for alkyl radicals of this kind are methyl, ethyl, n-propyl, isopropyl, n-butyl, iso-butyl, tert-butyl etc.

The term "alkylene" denotes a straight-chain or branched, bivalent hydrocarbon radical with 1 to 18 carbon atoms. Examples of such alkylene radicals are methylene, ethylene, 1,3-propandiyl, 1,6-hexamethylene etc.

The term "cycloalkylene" denotes a bivalent, cyclical alkyl radical with 5 or 6 carbon atoms. Examples of such cyclic alkylene radicals are cyclopentenyl and cyclohexenyl.

The term "arylalkylene" denotes an at least bivalent, aryl-aliphatic radical with at least 8 to 18 carbon atoms, wherein aryl denotes an aromatic hydrocarbon radical, e.g. phenyl, naphthyl or anthryl, and alkylene is defined as above. The linking in accordance with the general formula (I) is achieved with arylalkylene groups via the alkylene group.

Especially preferred 4-methylene-1,3-dioxolanes in accordance with the invention are:

1,3-bis-(4-methylene-1,3-dioxolane-2-yl)propane,
1,2-bis-(2-methyl-4-methylene-1,3-dioxolane-2-yl)ethane,
2,2'-bis-[4-methylene oxyphenyl-(4-methylene-1,3-dioxolane-2-yl)]propane,
bis-(4-methylene-1,3-dioxolane-2-yl)methane,
1,5-bis-(4-methylene-1,3-dioxolane-2-yl)pentane,
1,6-bis-(4-methylene-1,3-dioxolane-2-yl) hexane,
bis-(4-methylene-1,3-dioxolane-2-yl)methylether,
1,3-bis-[(4-methylene-1,3-dioxolane-2-yl)methylene oxy]propane,
tetrakis-[(4-methylene-1,3-dioxolane-2-yl)methylene oxy]neopentane,
1,4-bis-(4-methylene-1,3-dioxolane-2-yl)cyclohexane,
1,2-bis-[(4-methylene-1,3-dioxolane-2-yl)methylene oxy]ethane,
2,2'-bis-[(4-methylene-1,3-dioxolane-2-yl)methylene oxy]ethylether,
1,4-bis-[(4-methylene-1,3-dioxolane-2-yl)ethenyl]benzene,
1,3-bis-[(4-methylene-1,3-dioxolane-2-yl)methylene oxy]benzene,
1,5-bis-[(4-methylene-1,3-dioxolane-2-yl)methylene oxy]naphthalene,
2,2-bis-[4-(4-methylene-1,3-dioxolane-2-yl)methylene oxyphenyl]propane,
bis-[4-(4-methylene-1,3-dioxolane-2-yl)methylene oxyphenyl]methane,
4,4'-bis-[(4-methylene-1,3-dioxolane-2-yl)methylene oxy]biphenyl,
2,6-bis-[(4-methylene-1,3-dioxolane-2-yl)methylene oxy]anthraquinone,
1,3,5-tris-[(4-methylene-1,3-dioxolane-2-yl)methylene oxy]benzene.

The 4-methylene-1,3-dioxolanes are produced by a process characterised in that 4-chloromethyl-1,3-dioxolanes of the general formula (II)

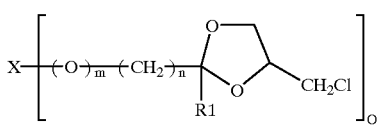

(II)

wherein R1, m, n, o and X are defined as above, are treated with a base at temperatures between 0° C. and 150° C. and the reaction product is isolated in accordance with a per se known process. By preference, the process is carried out at a temperature of 15° C. to 60° C.

Suitable bases are the alkaline and earth alkaline hydroxides such as sodium hydroxide, potassium hydroxide or calcium hydroxide, but also the alkaline salts of primary, secondary and tertiary alcohols, such as sodium methylate, sodium ethylate or potassium-tert-butylate. If these are not commercially available, the corresponding alkaline metals, alkaline metal hydrides or alkaline metal hydroxides may be dissolved in the corresponding alcohols. Most preferably potassium-tert-butylate is used as a base.

Treatment with a base may be implemented without a solvent. In general, however, it is more advantageous to use a solvent. The solvents may be alcohols, such as methanol, ethanol, isopropanol, 2-butanol or tert-butanol, but also ethers, such as ethylene glycol dimethyl ether, dioxane or tetrahydrofurane, but solvents such as dimethylsulfoxide or DMF are also suitable. However, esters of any kind are less suitable because, under the reaction conditions, they can saponify. Solvents which offer good solvent properties for the base used but which do not dissolve the metal chloride resulting from the reaction are particularly preferred. The isolation of the product is simplified in this manner.

Moreover, the present invention provides the chloromethyl compounds of the general formula (II) used for the production of the 4-methylene-1,3-dioxolanes according to the invention:

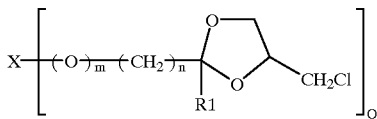

(II)

in which R1, X, n, m and o are defined as above.

Preferred chloromethyl compounds of the formula (II) are:

1,3-bis-(4-chloromethyl-1,3-dioxolane-2-yl)propane,
1,2-bis-(2-methyl-4-chloromethyl-1,3-dioxolane-2-yl)ethane,
2,2'-bis-[4-methylene oxyphenyl-(4-chloromethyl-1,3-dioxolane-2-yl)]propane,
bis-(4-chloromethyl-1,3-dioxolane-2-yl)methane,
1,5-bis-(4-chloromethyl-1,3-dioxolane-2-yl)pentane,
1,6-bis-(4-chloromethyl-1,3-dioxolane-2-yl)hexane,
bis-(4-chloromethyl-1,3-dioxolane-2-yl)methylether,
1,3-bis-[(4-chloromethyl-1,3-dioxolane-2-yl)methylene oxy]propane,
tetrakis-[(4-chloromethyl-1,3-dioxolane-2-yl)methylene oxy]neopentane,
1,4-bis-(4-chloromethyl-1,3-dioxolane-2-yl)cyclohexane,
1,2-bis-[(4-chloromethyl-1,3-dioxolane-2-yl)methylene oxy]ethane,
2,2'-bis-[(4-chloromethyl-1,3-dioxolane-2-yl)methylene oxy]ethylether,
1,4-bis-[(4-chloromethyl-1,3-dioxolane-2-yl)ethenyl]-benzene,
1,3-bis-[(4-chloromethyl-1,3-dioxolane-2-yl)methylene oxy]benzene,
1,5-bis-[(4-chloromethyl-1,3-dioxolane-2-yl)methylene oxy]naphthalene,
2,2-bis-[4-(4-chloromethyl-1,3-dioxolane-2-yl)methylene oxyphenyl]propane,
bis-[4-(4-chloromethyl-1,3-dioxolane-2-yl)methylene oxyphenyl]methane,
4,4'-bis-[(4-chloromethyl-1,3-dioxolane-2-yl)methylene oxy]biphenyl,
2,6-bis-[(4-chloromethyl-1,3-dioxolane-2-yl)methylene oxy]anthraquinone,
1,3,5-tris-[(4-chloromethyl-1,3-dioxolane-2-yl)methylene oxy]benzene.

The chloromethyl compounds of the general formula (II) are readily accessible from the reaction of aldehydes and ketones of the general formula (III),

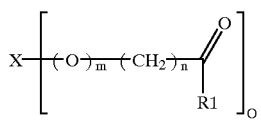

(III)

wherein R1, X, n, m and o are defined as above, with 3-chloro-1,2-propanediol. This reaction is catalysed by the presence of acids, such as p-toluene sulfonic acid or sulfuric acid. With some reactive aldehydes, catalysis can be entirely dispensed with.

These carbonyl compounds can also be reacted with epichlorhydrine in the presence of appropriate catalysts, such as Lewis acids; however, this does not always provide a clear advantage in yield.

The following are enumerated as examples of aldehydes and ketones of the general formula (III) which are suitable in accordance with the invention: glyoxal, glutardialdehyde, acetylacetone, acetonyl acetone, 2,3-hexanedione, 3,4-hexanedione, cyclohexane-1,4-dicarbaldehyde, ethylene glycol-bis-formylethylether, diglycolaldehyde.

Additional appropriate ketones of the general formula (III) can be obtained by etherification in accordance with WILLIAMSON of aromatic and aliphatic diols and polyols with chloroacetone. Preferred diols or polyols are ethylene glycol, diethylene glycol, triethylene glycol and polyethylene glycols, glycerol, pentaerythritol, propylene glycol, 1,3-propanediol, 1,4-dihydroxyanthraquinone, 2,6-dihydroxyanthraquinone, resorcinol, hydroquinone, 4,4'-dihydroxybiphenyl, bisphenol-A, bisphenol-F, 1,5-dihydroxynaphthalene, 2,7-dihydroxynaphthalene.

The water occurring in the reaction is removed by distillation, wherein the presence of an appropriate entrainer is advantageous. Non-water-miscible solvents such as toluene, chloroform or cyclohexane are particularly suitable for this purpose. In this context, it is not relevant whether the reagents dissolve homogeneously in the entrainer or whether two phases are formed. If no entrainer is used, it is advisable to apply a slight vacuum pressure to remove the water, provided the reagents used permit this.

Similarly, the chloromethyl compounds of the general formula (II) are accessible by the reaction of acetals and ketals of the general formula (IV),

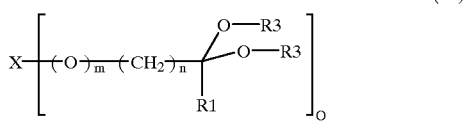

wherein R1 and X, n, m and o are defined as above and R3 denotes a methyl group or ethyl group, with 3-chloro-1,2-propanediol at a temperature of 25° C. to 150° C. This reaction is catalysed by the presence of acids, such as p-toluene sulfonic acid or sulfuric acid.

The following are enumerated as examples of acetals and ketals of the general formula (IV) which are suitable in accordance with the invention:
1,1,3,3-tetramethoxypropane, 1,1,6,6-tetramethoxyhexane, 1,1,8,8-tetramethoxyoctane.

Further appropriate acetals of the general formula (IV) are obtained by etherification in accordance with WILLIAMSON of aromatic and aliphatic diols and polyols with chloro- or bromoacetaldehyde dimethylacetal or -diethylacetal. Suitable diols or polyols are ethylene glycol, diethylene glycol, triethylene glycol and polyethylene glycols, 1,3-propanediol, glycerol, diglycerol, pentaerythritol, propylene glycol and polypropylene glycols. Phenols such as 1,4-dihydroxyanthraquinone, 2,6-dihydroxyanthraquinone, resorcinol, hydroquinone, 4,4'dihydroxybiphenyl, bisphenol-A, bisphenol-F, 4,4'-dihydroxydiphenylsulfone, 1,5-dihydroxynaphthalene, 2,7-dihydroxynaphthalene are very especially advantageous.

Under some circumstances, the appropriate acetals of the general formula (IV) are also accessible via Grignard reactions with appropriate halogen compounds.

The alcohol (methanol or ethanol) arising from the reaction of the acetals and ketals of the general formula (IV) with 3-chloro-1,2-propanediol can be removed very readily by distillation.

The above-mentioned 4-methylene-1,3-dioloxanes according to the invention may be copolymerized with maleimide compounds, such as N-isopropylmaleimide, N-butylmaleimide, N-cyclohexylmaleimide, N-phenylmaleimide and N-methoxyphenylmaleimide, wherein the copolymerization can be executed without the aid of a photo-initiator.

Furthermore, the 4-methylene-1,3-dioxolanes according to the invention can be used preferably as compositions capable of emission-free, photocationic cross-linking.

Namely, the invention provides compositions capable of emission-free, photocationic cross-linking which contain one or more of the 4-methylene-1,3-dioxolanes and one or more appropriate photo-initiators. While not limiting, the amount of the photo-initiator to be added is preferably 0.1 to 10% by weight, particularly preferably 1 to 5% by weight, based on the weight of the composition. In the invention, polymerization can be carried out without using other photopolymerizable monomers in combination. Hence, the above-described characteristics (a) to (f), especially the characteristic (e), are manifested more pronouncedly in the case where only the 4-methylene-1,3-dioxolanes according to the invention are used as a curable component.

The composition can contain other photo-cationic polymerizable monomers as needed so long as the effects of the invention are not impaired. Other photo-cationic polymerizable monomers which can be used in combination include vinyl ethers, such as methyl vinyl ether, hydroxymethyl vinyl ether and diethylene glycol divinyl ether; epoxy compounds, such as cyclohexene oxide, butyl glycidyl ether, hexyl glycidyl ether and bisphenol A epoxy resin; and oxetane compounds, such as 3-ethyl-3-hydroxymethyloxetane, 1,4-bis[(3-ethyl-3-oxetanylmethoxy)methyl]benzene and 3-ethyl-3-phenoxymethyloxetane. For the excellent reactivity of the 4-methylene-1,3-dioxolanes according to the invention, it is desirable that the amount of these monomers to be used is as small as possible.

The composition of the invention may further comprise a monofunctional 4-methylene-1,3-dioxolane. Since the monofunctional 4-methylene-1,3-dioxolane compounds are effective in suppressing release of volatile components, they can be added in an appropriate amount selected in accordance with the intended use. Examples of the monofunctional 4-methylene-1,3-dioxolane compound include 2-methyl-2-hydroxymethyl-4-methylene-1,3-dioxolane, 2-(1-hydroxymethyl-2-methylpropan-2-yl)-4-methylene-1,3-dioxolane, 2-methyl-2-ethoxycarbonylmethyl-4-methylene-1,3-dioxolane, 2-methyl-2-(ethyl 1-cyclopentenylcarboxylate-1-yl)-4-methylene-1,3-dioxolane, and 2-methyl-2-(ethyl propionate-3-yl)-4-methylene-1,3-dioxolane.

As the photo-initiator, any of commercially available photo-initiators can be used. In particular, triaryl sulfonium salts and diaryl iodonium salts are preferred.

As needed, the composition may contain additives appropriately selected in accordance with the intended use, such as inorganic fillers, organic fillers, coupling agents, tackifiers, antifoaming agents, plasticizers, antioxidants, ultraviolet absorbers, flame retardants, pigments, dyes, storage stabilizers, and the like. The composition may further contain non-reactive oligomers or resins, such as (meth) acrylic copolymers, styrene-(meth)acrylic copolymers, and liquid polybutadiene.

The use amounts of these optional components can be appropriately selected depending on the intended use.

The composition according to the present invention can be effectively used for printing inks, paper coatings, wood coatings, metal can coatings, protective coatings for plastics such as CDs and DVDs, coatings for light wrapping films, laminate adhesives, adhesives for DVDs, pressure-sensitive adhesives, transparent films, and the like. In particular, it should be noted that the composition is applicable to films and thin layers which have been difficult to produce by photo-cationic crosslinking reaction. As for the films, transparent films of the invention are especially preferred.

The transparent film of the invention is prepared by casting the composition into film and irradiating the cast film to proceed photo-cationic polymerization. Since the 4-methylene-1,3-dioxolanes of the invention crosslink rapidly either individually or as a combination thereof under photo-cationic conditions, it is desirable that no other photo-cationic polymerizable monomers be used in combination. The transparent films thus obtained are excellent in solvent resistance.

The present invention will be explained in greater detail with reference to the following Examples, but the invention should not be construed as being limited thereto.

PRODUCTION EXAMPLE 1

500 g (approx. 2.5 mol) of an approximately 50% aqueous glutardialdehyde solution, 600 g (5.5 mol) 3-chloro-1,2-propanediol and approx. 400 ml toluene are placed in a 2 liter flask fitted with a water separator and heated to boiling. After 3–4 hours, 340 ml water will have been separated. The mixture is cooled to room temperature, washed twice with approximately 150 ml water and dried over Na$_2$SO$_4$. The toluene is removed in the rotation evaporator and the residue is distilled. 627 g (88%) 1,3-bis(4-chloromethyl-1,3-dioxolane-2-yl)propane are obtained: boiling point: 138–140° C. (5×10$^{-3}$ mbar); GC: 3 isomers; MS: m/e=283, 249, 235, 191, 147, 121, 93, 75, 57, 41.

In a 4-liter surface ground flask, 370 g (3.3 mol) potassium-tert.-butylate are dissolved in 1400 ml dry THF at room temperature. 439 g (1.54 mol) 1,3-bis-(4-chloromethyl-1,3-dioxolane-2-yl) propane are added dropwise to the resulting clear solution in such a manner that the temperature of the reaction solution remains below 50° C. After completion of this stage, the reaction solution is stirred for a further 24 hours at room temperature, heated again for 2 hours to 50° C and the THF is separated in the rotation evaporator. The residue is dissolved in approximately 500 ml water; the organic phase is separated, and this is then dried over Na$_2$SO$_4$ and distilled. A yield of 195 g (60%) 1,3-bis(4-methylene-1,3-dioxolane-2-yl)propane is obtained: boiling point: 82–84° C. (10$^{-2}$ mbar); IR: 3363 cm$^{-1}$ and 1689 cm$^{-1}$ (double bond, vinyl ether); MS: m/e= 212 (M$^+$), 184, 169, 155, 141, 125, 111, 99, 85, 57, 43.

PRODUCTION EXAMPLE 2

The suspension of 9.6 g (0.4 mol) sodium hydride in 150 ml dry DMAc is placed into a conical flask and the solution of 45.6 g (0.2 mol) bisphenol-A in 100 ml dry DMAc is slowly added. To complete the formation of the sodium salt, the reaction solution is heated to approximately 80° C. When the evolution of gas has terminated, 62 g (0.5 mol) chloracetaldehyde dimethyl acetal are added dropwise, and the mixture is stirred for 5 hours at 140–150° C. The mixture is then cooled to room temperature, poured into 1000 ml water to which 10 g NaOH have been added, and extracted three times, in each case with 100 ml petroleum ether. After drying and removal of the solvent, a yield of 77 g (95%) bisphenol-A-4,4'-bis(2,2,2',2'-tetramethoxy)ethylether will remain. GC: purity >98%; MS: m/e=404 (M$^+$), 389, (M-15), 232, 197, 165, 135, 119, 89, 75, 59, 47; IR: 1078 cm$^{-1}$ and 1137 cm$^{-1}$ (acetal).

22 g (54 mmol) bisphenol-A-4,4'-bis(2,2,2'2'-tetramethoxy)ethylether, 16.6 g (0.15 mol) 3-chloro-1,2-propanediol and 0.1 g p-TSA are placed into a 100 ml flask fitted with stirring paddles and distillation bridge and heated to approx. 90° C. The resulting methanol is distilled off. After 6.9 ml have been transferred, the raw product is cooled, dissolved in methylene chloride and treated with dilute, aqueous NaOH. The organic phase is separated, dried over K$_2$CO$_3$ and the solvent is removed. A yield of 27.3 g (95%) 2,2-bis-[4-(4-chloromethyl-1,3-dioxolane-2-yl) methylene oxyphenyl]propane is obtained. MS: m/e=496 (M$^+$), 481 (M-15), 403, 347, 269, 207, 135, 121, 93, 75, 57, 43; melting point (ethanol): 70° C.; IR: 1054 cm$^{-1}$ and 1148 cm$^{-1}$ (acetal)

Using a glass beaker, 16.8 g (0.15 mol) potassium-tert.-butylate are dissolved in approx. 50 ml dry THF and the chloromethyl compound, diluted with approx. 50 ml THF, is added in such a manner that the temperature remains below 50° C. The reaction solution is then stirred for 16 hours at room temperature, poured into approx. 600 ml water and extracted three times with approx. 50 ml petroleum ether. The organic phase is separated, dried over Na$_2$SO$_4$, and the solvent is removed in the rotation evaporator. A yield of 21 g (95%) 2,2-bis-[4-(4-methylene-1,3-dioxolane-2-yl)-methylene oxyphenyl]-propane is obtained with a purity of >98%, as a slightly yellow, viscous fluid. (GC). MS: m/e= 424 (M$^+$), 409 (M-15), 353, 311, 255, 213, 159, 135, 119, 99, 85, 57; IR: 1689 cm$^{-1}$ (vinyl ether).

PRODUCTION EXAMPLE 3

10.8 g (0.2 mol) sodium methylate in 100 ml DMF are placed in a conical flask and the solution of 11 g (0.1 mol) resorcinol in 50 ml DMF is slowly added. The reaction solution is heated to 80° C. and 39.4 g (0.2 mol) bromacetaldehyde diethylacetal are added slowly, dropwise. The reactants are stirred for 10 hours at 80° C., poured into 500 ml water to which 5 g NaOH have been added, and extracted with petroleum ether. After drying and removal of the solvent, a yield of 17.6 g (51%) 1,3-bis(2,2-diethoxyethyloxy)benzene is obtained. GC: purity>85%; MS: m/e=342 (M$^+$), 296, 251, 205, 159, 133, 103, 92, 75, 61, 47.

In accordance with Example 2, 17.6 g (51 mmol) 1,3-bis (2,2-diethoxyethyloxy)benzene are heated with 11.1 g (0.1 mol) 3-chloro-1,2-propanediol and 0.1 g p-TSA to 150° C. and the resulting ethanol is distilled off. After the work-up, a yield of 17.5 g (92%) 1,3-bis[(4-chloromethyl-1,3-dioxolane-2-yl)-methylene oxy]benzene is obtained. IR: 1189 cm$^{-1}$, 1143 cm$^{-1}$, 1049 cm$^{-1}$ (acetal bands); GC: purity >90% (3 isomers); MS: m/e=378 (M$^+$), 343, 269, 243, 219, 159, 134, 121, 93, 75, 57, 43.

Elimination is also carried out in a similar matter to Example 2 with potassium-tert.-butylate in THF. After work-up and distillation, a yield of 9 g (58%) 1,3-bis[(4-methylene-1,3-dioxolane-2-yl)methylene oxy]benzene is obtained. Boiling point: 188° C. (5×10$^{-3}$ mbar); IR: 1689 cm$^{-1}$ (double bond, vinyl ether); GC: purity >95% (2 isomers); MS: m/e=306 (M$^+$), 250, 232, 206, 177, 159, 134, 107, 98, 85, 76, 57.

PRODUCTION EXAMPLE 4

According to Example 1, 100 g (0.87 mol) acetonylacetone and 199 g (1.8 mol) 3-chloro-1,2-propanediol are boiled together with 0.5 g p-TSA and approximately 150 ml cyclohexane in the water separator until no more water is transferred. After distillation, a yield of 200 g (76%) 1,2-bis-(2-methyl-4-chloromethyl-1,3-dioxolane-2-yl)ethane is obtained. Boiling point: 192° C. (15 mbar); IR: 1115 and 1078 cm$^{-1}$ (acetal bands); GC: purity >99.5% (3 isomers); MS: m/e=283 (M-15), 249, 233, 191, 177, 163, 149, 135, 123, 99, 75, 55, 43.

As in the preceding examples, elimination is carried with tert.-BuOK in THF. After work-up and distillation, 1,2-bis-(2-methyl-4-methylene-1,3-dioxolane-2-yl)ethane is obtained in a yield of 69%. Boiling point: 70° C (10$^{-2}$ mbar); IR: 1687 cm$^{-1}$ (double bond); GC: purity>99%; MS: m/e= 226 (M$^+$), 211 (M-15), 183, 165, 155, 125, 115, 99, 85, 71, 55, 43.

PRODUCTION EXAMPLE 5

As in the case of Example 3, 16.5 g resorcinol (0.15 mol), 27.6 g potassium carbonate (0.2 mol) and 0.1 g lithium iodide are placed in a conical flask in approximately 100 ml DMF, and 27.8 g (0.3 mol) chloracetone are added slowly, dropwise. The reaction is slightly exothermic. The mixture is then stirred for approx. 1 hour at room temperature and then heated to approx. 80° C. After 4 hours, the reaction mixture is poured into 500 ml iced water to which approx. 3 g NaOH have been added and extracted with methylene chloride. The extract is washed with water, dried over sodium sulfate, and the solvent is removed. The resulting 1,3-bis-(acetonyloxy)benzene is 98% according to GC, so that re-crystallisation is not required. Yield: 15 g (45%); IR: 1723 cm$^{-1}$ (C=O), 1154 cm$^{-1}$ (C—O—C); MS: m/e=222 (M$^+$), 204, 179, 151, 137, 123, 107, 92, 76, 57, 43.

Following this, 16.6 g (0.15 mol) 3-chloro-1,2-propanediol, 0.1 g p-toluene sulfonic acid and 50 ml toluene are added to 15 g (68 mmol) 1,3-bis-(acetonlyoxy)benzene, and the reaction mixture is boiled in the water separator until no more water is transferred. Then, the reaction mixture is washed with weakly alkaline water and dried over sodium sulfate. After removing by rotary evaporator of the solvent, a yield of 26 g (95%) 1,3-bis-[(2-methyl-4-chloromethyl-1,3-dioxolane-2-yl)methylene oxy]benzene is obtained. GC: purity approximately 90%; IR: 1181 cm$^{-1}$, 1155 cm$^{-1}$, 1064 cm$^{-1}$ (ketal); MS: m/e=406 (M$^+$), 391 (−15), 341, 297, 281, 207, 187, 162, 149, 135, 121, 75, 57, 43.

Elimination is carried out in a similar manner to the preceding examples with potassium-tert,-butylate in THF. After conversion, a yield of 13 g (58%) 1,3-bis-[(2-methyl-4-methylene-1,3-dioxolane-2-yl)methylene oxy]benzene is obtained. IR: 1687 cm$^{-1}$ (vinyl ether); MS: m/e=334 (M$^+$), 261, 222, 205, 187, 155, 133, 121, 99, 76, 57, 43.

PRODUCTION EXAMPLE 6

72 g (0.45 mol) 1,5-dihydroxynaphthalene are dissolved in 400 ml DMAc while heating in a three-necked flask fitted with a dropping funnel, internal thermometer, column and distillation cap. Then, at an internal temperature of 110–130° C., 178 g (1.1 mol) of a 30% solution of sodium methanolate in methanol are added dropwise and the resulting methanol is distilled off continuously via the column. When all the methanol has been transferred, 136 g (1.1 mol) chloracetaldehyde dimethylacetal is added in one portion, and the reaction is allowed to continue for approximately 3 hours at 130° C. Following this, the reaction mixture is cooled to 80° C., filtered while still warm, and the filtrate is poured onto 1000 g iced water to which 15 g NaOH have been added. The precipitate is filtered off, washed thoroughly with water and then dried under vacuum at 60° C. A yield of 80 g (53%) 1,5-bis-(2,2'-dimethoxyethoxy)naphthalene is obtained. Melting point: 117° C.; IR (KBr): 1273 cm$^{-1}$ (ether); MS: m/e=336 (M$^+$), 304, 273, 241, 215, 197, 185, 171, 160, 115, 89, 75, 59, 43.

78 g (0.23 mol) 1,5-bis-(2',2'-dimethoxyethoxy) naphthalene are mixed with 77 g (0.7 mol) 3-chloro-1,2-propanediol and 0.5 g p-TSA and then heated together with 300 ml toluene to gentle boiling. The resulting methanol is removed via a column. When the reaction has ended, the warm reaction mixture is washed with aqueous NaOH, dried over Na$_2$SO$_4$ and evaporated in the rotary evaporator. Under cooling, 1,5-bis-[(4-chloromethyl-1,3-dioxolane-2-yl)methylene oxy]-naphthalene crystallises from the toluene. After washing with MeOH, a yield of 46 g (47%) is obtained; melting point: 99° C.; IR: 1273 cm$^{-1}$, 1176 cm$^{-1}$, 1154 cm$^{-1}$, 1089 cm$^{-1}$ (ether and acetal bands); MS: m/e= 428 (M$^+$), 394, 319, 294, 278, 253, 227, 197, 184, 171, 155, 135, 121, 107, 93, 75, 57, 43.

30 g (0.3 mol) sodium-tert-butylate are dissolved in 250 ml dry THF under gentle warming, and the solution of 41 g (0.096 mol) 1,5-bis[(4-chloromethyl-1,3-dioxolane-2-yl) methylene oxy]naphthalene in 150 ml warm THF is added dropwise in such a manner that the reaction mixture only boils gently. The reaction is allowed to continue for a further 4 hours at approx. 60° C. The product is then poured into 1500 ml iced water and the precipitate is filtered off. This is washed with water and recrystallised from THF. A yield of 25 g (73%) 1,5-bis-[(4-methylene-1,3-dioxolane-2-yl) methylene oxy]naphthalene is obtained.

Melting point: 154° C.; IR (KBr): 1688 cm$^{-1}$ (vinyl ether); MS: m/e=356 (M$^+$), 281, 253, 207, 184, 160, 131, 115, 98, 85, 73, 57, 43.

CROSS-LINKING EXAMPLES

In Cross Linking Examples 1 to 6 and the Comparative Examples 1 and 2, the substances and/or substance mixtures given in Table 1 were mixed with 5 wt. % FX-512™ (50% solution of triphenyl sulfonium hexafluorophosphate in γ-butyrolactone, 3M Netherlands), applied as a 12 μm thick film onto glass slides and irradiated with a UV lamp (Fusion F300S™, "D-Spot", Fusion UV Curing Systems, USA) at a belt speed of 50 m/min until the applied film was no longer adhesive. Methylene dioxolanes with low melting point were melted before cross-linking; compounds with a higher melting point were dissolved in liquid methylene-dioxolanes and cross-linked as mixtures. In the mixtures, the methylene dioxolanes were contained in equal parts by weight in each case. The hardness of the films formed (measured using the corresponding Wolff-Wilborn pencil-hardness scale) and their resistance to methylene ketone (MEK) (measured by pressure-free rubbing with an MEK-impregnated cellulose cloth) were measured after 24 hours. The results are shown in Table 1.

The comparative examples clearly demonstrate that methylene dioxolanes only cross-link without emissions if the 2-position is not substituted directly with an aromatic.

TABLE 1

Photocationic cross-linking of 4-methylene-1,3-dioxolanes

| No. | Substance (mixture)[1] | Hardness | Resistance to MEK[2] | Odour |
|---|---|---|---|---|
| Examples |
| 1 | A | 2H | >75 | none |
| 2 | B | H | >75 | none |
| 3 | C | 3H | >75 | none |
| 4 | A + C | 2H | >75 | none |
| 5 | A + B | HB | >75 | none |
| 6 | B + C | 2H | >75 | none |
| Comparative examples |
| 1 | A + D + E | 3H | >75 | like anisum |
| 2 | D + E | 3H | >75 | like anisum |

[1]The symbols denote the substances provided below.
[2]Number of strokes after which no degradation of the film was yet identifiable.

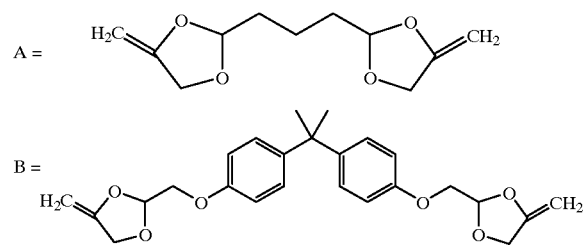

-continued

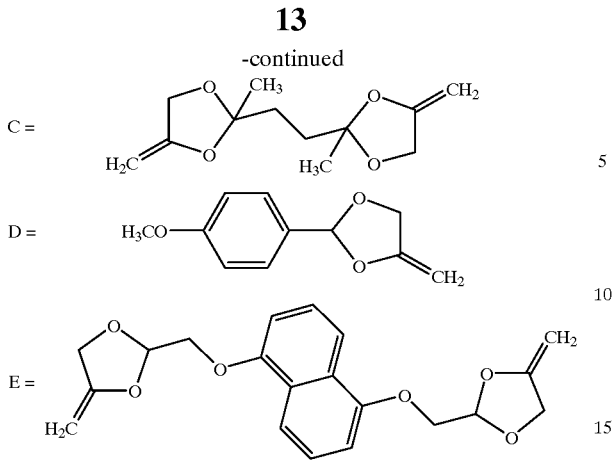

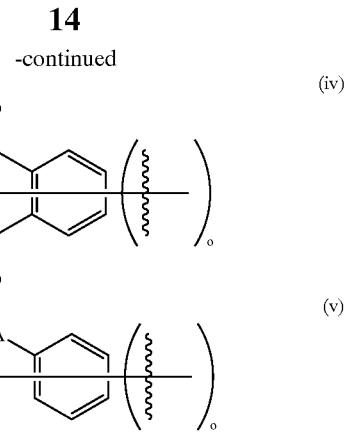

While the invention has been described in detail and with reference to specific examples thereof, it will be apparent to one skilled in the art that various changes and modifications can be made therein without departing from the spirit and scope thereof.

What is claimed is:

1. A 4-methylene-1,3-dioxolane compound of the general formula (I):

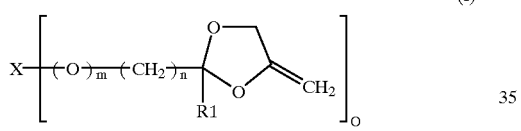

wherein R1 denotes hydrogen, $C_5$–$C_6$-cycloalkyl or $C_1$–$C_4$-alkyl; m and n, which may be the same or different, denote 0 or 1, wherein m≦n, o denotes 2, 3 or 4 depending on the valency of the group X; and X denotes a straight-chain when said m denotes 1, or branched $C_1$–$C_{18}$-alkylene, $C_5$–$C_6$-cycloalkylene, $C_8$–$C_{18}$-arylalkylene, —$CH_2(OCH_2CH_2)_pOCH_2$—, —$CH_2(OCH(CH_3)CH_2)_pOCH_2$—, wherein p is an integer from 0 to 100, or a group selected from wherein q≦(6-o), r≦(8-o), R2 denotes H or a $C_1$–$C_4$-alkyl group and A denote a single bond or denotes —C(CH$_3$)2—, —C(CF$_3$)2—, —CH$_2$—, —SO$_2$— or —(C═O)—, and wherein the 2-position of the 1,3-dioxolane ring is not linked directly to an aromatic group.

2. A 4-methylene-1,3-dioxolane compound, selected from the group consisting of:
1,3-bis-(4-methylene-1,3-dioxolane-2-yl)propane,
1,2-bis-(2-methyl-4-methylene-1,3-dioxolane-2-yl)ethane,
2,2'-bis-[4-methylene oxyphenyl-(4-methylene-1,3-dioxolane-2-yl)]propane,
bis-(4-methylene-1,3-dioxolane-2-yl)methane,
1,5-bis-(4-methylene-1,3-dioxolane-2-yl)pentane,
1,6-bis-(4-methylene-1,3-dioxolane-2-yl) hexane,
bis-(4-methylene-1,3-dioxolane-2-yl)methylether,
1,3-bis-[(4-methylene-1,3-dioxolane-2-yl)methylene oxy]propane,
tetrakis-[(4-methylene-1,3-dioxolane-2-yl)methylene oxy]neopentane,
1,4-bis-(4-methylene-1,3-dioxolane-2-yl)cyclohexane,
1,2-bis-[(4-methylene-1,3-dioxolane-2-yl)methylene oxy]ethane,
2,2'-bis-[(4-methylene-1,3-dioxolane-2-yl)methylene oxy]ethylether,
1,4-bis-[(4-methylene-1,3-dioxolane-2-yl)ethenyl]benzene,
1,3-bis-[(4-methylene-1,3-dioxolane-2-yl)methylene oxy]benzene,
1,5-bis-[(4-methylene-1,3-dioxolane-2-yl)methylene oxy]naphthalene,
2,2-bis-[4-(4-methylene-1,3-dioxolane-2-yl)methylene oxyphenyl]propane,
bis-[4-(4-methylene-1,3-dioxolane-2-yl)methylene oxyphenyl]methane,
4,4'-bis-[(4-methylene-1,3-dioxolane-2-yl)methylene oxy]biphenyl,
2,6-bis-[(4-methylene-1,3-dioxolane-2-yl)methylene oxy]anthraquinone,
1,3,5-tris-[(4-methylene-1,3-dioxolane-2-yl)methylene oxy]benzene.

3. A process for the production of a 4-methylene-1,3-dioxolane compound of the general formula (I):

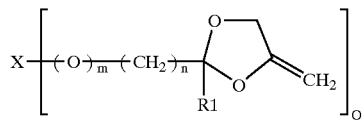
(I)

wherein R1 denotes hydrogen, $C_5$–$C_6$-cycloalkyl or $C_1$–$C_4$-alkyl; m and n, which may be the same or different, denote 0 or 1, wherein $m \leq n$, o denotes 2, 3 or 4 depending on the valency of the group X; and X denotes a C—C single bond, straight-chain or branched $C_1$–$C_{18}$-alkylene, $C_5$–$C_6$-cycloalkylene, $C_8$–$C_{18}$-arylalkylene, —$CH_2(OCH_2CH_2)_pOCH_2$—, —$CH_2(OCH(CH_3)CH_2)_pOCH_2$—, wherein p is an integer from 0 to 100, or a group selected from

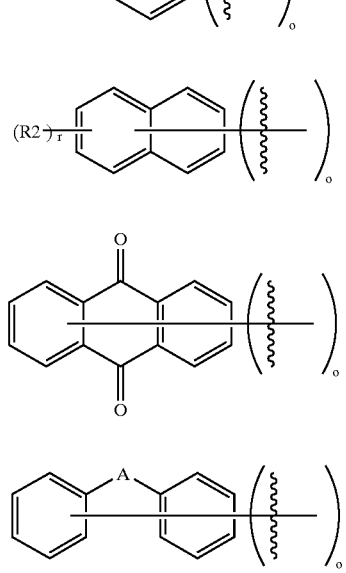

wherein $q \leq (6-o)$, $r \leq (8-o)$, R2 denotes H or a $C_1$–$C_4$-alkyl group and A denotes a single bond or denotes —$C(CH_3)2$—, —$C(CF_3)2$—, —$CH_2$—, —$SO_2$— or —(C=O)—, and wherein the 2-position of the 1,3-dioxolane ring is not linked directly to an aromatic group, the process comprising the steps of:
treating a 4-chloromethyl-1,3-dioxolane compound of the genera formula (II):

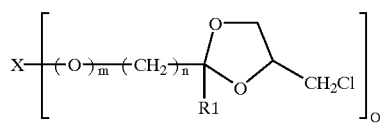
(II)

wherein R1, m, n, o and X have the same meaning, respectively, as those defined for general formula (I) above,
with a base at a temperature from 15° C. to 60° C. to obtain a reaction product; and
isolating the reaction product in accordance with a per se known process.

4. The process according to claim 3, wherein the treatment is implemented in the presence of a solvent.

5. The process according to claim 4, wherein the solvent is an alcohol, an ether, dimethylsulfoxide or dimethylformamide.

6. A process for the production of a 4-methylene-1,3-dioxolane compound of the general formula (I):

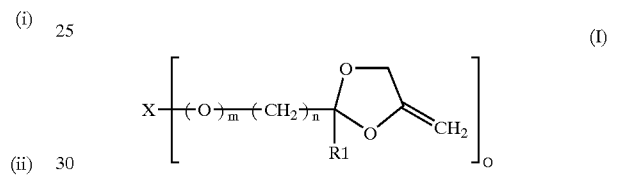
(I)

wherein R1 denotes hydrogen, $C_5$–$C_6$-cycloalkyl or $C_1$–$C_4$-alkyl; m and n which may be the same or different, denote 0 or 1, wherein $m \leq n$, o denotes 2, 3 or 4 depending on the valency of the group X; and X denotes a C—C single bond, straight-chain or branched $C_1$–$C_{18}$-alkylene, $C_5$–$C_6$-cycloalkylene, $C_8$–$C_{18}$-arylalkylene, —$CH_2(OCH_2CH_2)_pOCH_2$—, —$CH_2(OCH(CH_3)CH_2)_pOCH_2$—, wherein p is an integer from 0 to 100, or a group selected from

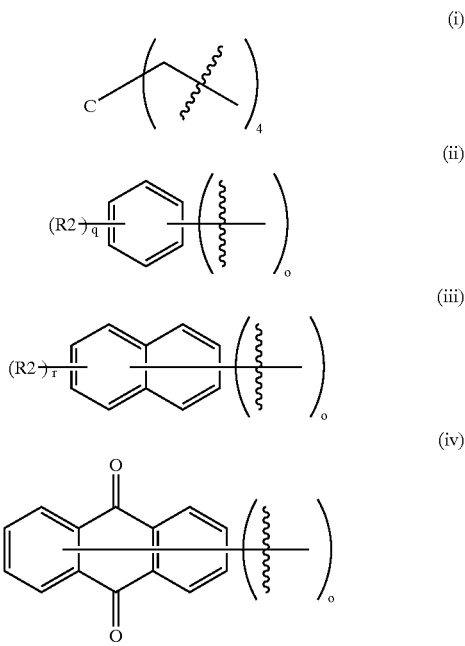

-continued (v)

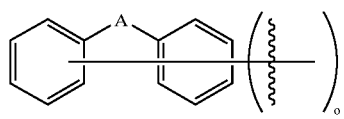

wherein q≦(6-o), r≦(8-o), R2 denotes H or a $C_1$–$C_4$-alkyl group and A denotes a single bond or denotes —C(CH$_3$)2—, —C(CF$_3$)2—, —CH$_2$—, —SO$_2$— or —(C=O)—, and wherein the 2-position of the 1,3-dioxolane ring is not linked directly to an aromatic group, the process comprising the steps of:

treating a 4-chloromethyl-1,3-dioxolane compound of the genera formula (II):

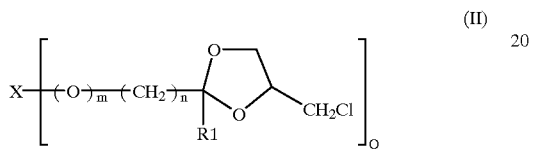

(II)

wherein R1, m, n, o and X have the same meaning, respectively, as those defined for general formula (I) above, with a base at a temperature from 0° C. to 150° C. to obtain a reaction product; and isolating the reaction product in accordance with a per se known process, wherein the base is potassium-tert.-butylate.

7. A composition capable of emission-free, photocationic cross-linking comprising at least one 4-methylene-1,3-dioxolane compound according to claim 1 and at least one photo-initiator.

8. The composition according to claim 7, wherein the photo-initiator comprises a triaryl sulfonium salt or a diaryl iodonium salt.

9. A transparent film obtained from a composition according to claim 7 or 8.

10. The 4-methylene-1,3-dioxolane compound according to claim 1, being 2,2'-oxybismethylene-bis-(4-methylene-1,3-dioxolane).

11. The 4-methylene-1,3-dioxolane compound according to claim 1, being the product of the reaction of diglycolaldehyde and 3-chloro-1,2-propandiol.

12. The 4-methylene-1,3-dioxolane compound according to claim 1, being 2,2'-oxybis(ethyleneoxymethylene)-bis-(4-methylene-1,3-dioxolane).

13. The 4-methylene-1,3-dioxolane compound according to claim 1, made by the steps of synthesizing an acetal compound by reacting a compound selected from the group consisting of chloroacetaldehyde dimethylacetal, bromoacetaldehyde dimethylacetal, chloroacetaldehyde diethylacetal and bromoacetaldehyde diethyl acetal with diethylene glycol to form a resulting acetal compound followed by reacting said resulting acetal compound with 3-chloro-1,2-propandiol to give a 4-chloromethyl-1,3-dioxolane compound;

treating the obtained 4-chloromethyl-1,3-dioxolane compound with a base at a temperature from 15° C. and 60° C. to obtain a reaction product; and isolating the reaction product in accordance with a per se known process.

14. The process according to claim 3, wherein the process comprises the steps of 1) reacting a compound of the general formula (III):

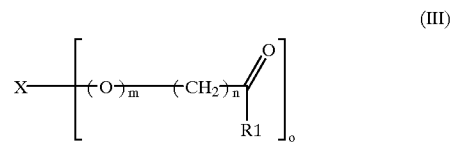

(III)

wherein R1, m, n, o and X have the same meanings as those defined for general formula (I) in claim 6, respectively, with 3-chloro-1,2-propanediol to give a 4-chloromethyl-1,3-dioxolane compound of the general formula (II):

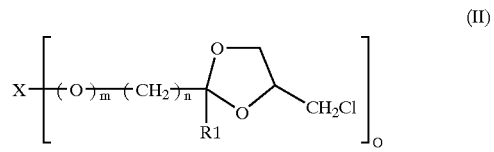

(II)

wherein R1, m, n, o and X have the same meaning, respectively, as those defined for general formula (I) in claim 6;

2) removing the resulting reaction water by distillation to isolate the 4-chloromethyl-1,3-dioxolane compound;

3) treating the obtained 4-chloromethyl-1,3-dioxolane compound with a base at a temperature from 15° C. and 60° C. to give a 4-methylene-1,3-dioxolane compound of the general formula (I):

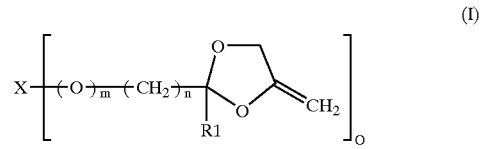

(I)

wherein R1, m, n, o and X have the same meanings, respectively, as those defined for general formula (I) in claim 6; and 4) isolating the 4-methylene-1,3-dioxolane compound in accordance with a per se known process.

15. The process according to claim 14, wherein the step 1) is carried out in the presence of a catalyst.

16. The process according to claim 14 or 15, wherein an entrainer is used in the step 1).

17. The process according to claim 3, wherein the process comprises the steps of 1) treating an acetal of the general formula (IV):

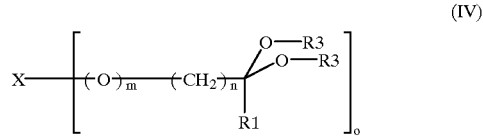

(IV)

wherein R1, m, n, o and X have the same meanings as those defined for general formula (I) in claim 6, respectively, and R3 denotes a methyl or ethyl group, with 3-chloro-1,2-propanediol in the presence of an acidic catalyst at a temperature from 25° C. to 150° C. to give a 4-chloromethyl-1,3-dioxolane compound of the general formula (II):

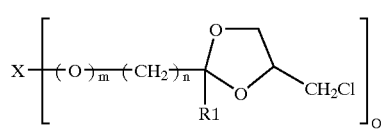

wherein R1, m, n, o and X have the same meaning, respectively, as those defined for general formula (I) in claim 6;

2) removing the resulting alcohol by distillation;
3) treating the obtained 4-chloromethyl-1,3-dioxolane compound with a base at a temperature from 15° C. and 60° C. to give a 4-methylene-1,3-dioxolane compound of the general formula (I):

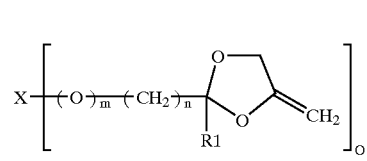

wherein R1, m, n, o and X have the same meanings, respectively, as those defined for general formula (I) in claim 6; and 4) isolating the 4-methylene-1,3-dioxolane compound in accordance with a per se known process.

* * * * *